United States Patent [19]

Strawn

[11] Plant 4,637

[45] Feb. 3, 1981

[54] MINIATURE ROSE PLANT

[76] Inventor: Leslie E. Strawn, 10422 Morningside Ave., Garden Grove, Calif. 92643

[21] Appl. No.: 94,574

[22] Filed: Nov. 15, 1979

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant characterized by two-toned rose pink buds and flowers of distinctive form and further identified by the neat dwarf, compact plant.

1 Drawing Figure

1

The present invention relates to a new and distinct variety of hardy, dwarf, bush type rose plant of the miniature class; the variety being primarily characterized—as to novelty—by the two-toned rose pink buds and flowers which in general color effect are similar to Pink Cameo (miniature—U.S. Plant Pat. No. 1,451 expired).

The variety is further characterized by:

The unique buds and flowers.

An abundance of bloom, with flowers borne one to a stem. No side buds.

Light rose fragrance.

A plant which is vigorous, of a rounded somewhat spreading shape with small semi-glossy (to matt) foliage with pointed leaflets; the buds and flowers being similar in form and size to Peaches 'N Cream (miniature—U.S. Plant Pat. No. 4,278).

The plant, which has a normal height of 12 to 14 inches, can easily be maintained at a lesser height by occasional trimming.

A plant which grows and blooms satisfactorily both in greenhouse and outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between Attraktion (floribunda—non patented) as the seed parent and Sheri Anne (miniature—U.S. Plant Pat. No. 3,826) as the pollen parent.

Subsequent to origination of the variety I successfully asexually reproduced it in my garden, located as foresaid (also propagated by Pixie Treasures Rose Nursery, 4121 Prospect Ave., Yorba Linda, Orange County, Calif., by cuttings as well as by budding; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

2

*Variety name.*—Birthday Party.

Flowers borne: Singly on upright slender stems.

Quantity of bloom: Abundant; both outdoors and in greenhouse.

Bud:

*Peduncle.*—Medium length; slender but sturdy; erect; slight curve; light green, sometimes tinted bronze (outdoors); Hairs—few, very tiny.

*Before calyx breaks.*—Size—small. Form—pointed; medium long; with foliaceous parts extending beyond tip of bud equal to one third of its length. Color—medium green.

*As calyx breaks.*—Color of guard petals showing near Spinel Red 0023. Opening—opens well in all weather.

Bloom:

*Size when fully open.*—Small, averaging about 4 cm (1½").

*Petalage.*—Double—averaging about 25 to 30 petals, arranged regularly, plus a few small petaloids.

*Form.*—Full at first, becoming rounded with high center, with petals rolled loosely outward in a round symmetrical effect.

Petals: Fairly thick; satiny on inside and on outside surfaces.

*Shape.*—Outside petals—broad heart shaped with notched tip and wedge shaped base; intermediate petals—medium broad heart shaped with wedge shaped base; inside petals—slightly smaller in width, notched, some curved with a more pointed base.

Color: One half to three quarters open flower from a plant grown outdoors at Pixie Treasures Rose Nursery, Yoba Linda, Calif., October 1979.

*Outside petal.*—Outside surface—near Neyron Rose 623 on the outer third of area with veining and center area near Rose Mader 23/1; base tipped with a very small spot of greenish white. Inside surface near Neyron Rose 623/2 with near Neyron Rose 623 towards base, base having a very small spot of greenish white.

*Intermediate petal.*—Outside surface—near Neyron Rose 623/1 on outer half of area with slight veining and center area near Rose Madder 23/1; base tipped with a very small spot of greenish white. Inside surface—near Neyron Rose 623/3 with a small area near base of near Neyron Rose 623/1, base tipped with a very small spot of greenish white.

*Inner petal.*—Outside surface—very close in color to intermediate petal; Inside surface—very close in color to intermediate petal; few may have, or may not have a small streak of near white.

General color effect:

*Newly opened flowers.*—Symmetrical arrangement of light pink petals with deeper pink to the center of bloom.

*Three days open.*—Color similar to newly open flower with less of the deep pink showing, petaloids covering stamens.

Behavior: Opens well in all weather. Spent petals tend to hang on for a time, then old flowers drop (separates at base of peduncle). Flower longevity (October 1979)—plant in pot 4–5 days or longer; in the ground may last longer. Cut flowers at livingroom temperature 3–4 days or longer.

Reproductive organs:

*Stamens.*—Vary 15–30.

*Filaments.*—Golden yellow, uneven lengths.

*Anthers.*—Golden yellow, introrse, 1 mm.

*Pollen.*—Moderate amount.

*Pistils.*—Project above disc.

*Styles.*—Several, 2 mm, bunched, light greenish yellow tinted bronze.

*Ovaries.*—Enclosed in calyx.

*Hips.*—Rarely formed.

*Sepals.*—Permanent; spear shaped, reflexed.

*Seed.*—Few if any.

Foliage:

*Leaves.*—Compound of five or seven leaflets—averaging 4 to 7 cm in length; quite small; leathery; semi-glossy.

*Leaflets.*—Shape—broad lanceolate; broad apex; short petiolule. Margin serrate.

*Rachis.*—Medium strength; upper side grooved and bearing many tiny short hairs; underside few hooked thorns and a few hairs.

*Stipules.*—Medium length; slender pointed auricles bearing tiny hairs, pointed outward about 45 degrees. Smooth sides.

*Color.*—Medium green with serrated edges and rachis tending to be reddish bronze, older leaves lose their bronze tint.

Growth:

*Habit.*—Dwarf; bushy, rounded; much branched.

*Growth.*—Vigorous; internodes short.

*Canes.*—Medium slender; sturdy.

*Main stems.*—Color — light to medium green.

*Branches.*—Light to medium green, tinted bronze.

*Thorns.*—Needle shaped, set at right angles to branch, sometimes slightly declining; color—light tan; very few.

*Young shoots.*—Reddish green.

The miniature rose plant and its flowers as herein described may vary in slight detail due to climatic, soil and cultural conditions under which the variety may be grown.

The following is claimed:

1. A new and distinct variety of miniature rose plant of hardy, dwarf, bushy, rounded, much branched habit, substantially as illustrated and described, characterized by buds and flowers which are in a color hue similar to Pink Cameo (miniature—U.S. Plant Pat. No. 1,451 expired) but giving a color effect of light pink flowers with darker pink centers, and resembling Peaches 'N Cream (miniature—U.S. Plant Pat. No. 4,278) in form and size, having buds and flowers of a distinct and unique appearance as compared to other miniature roses, said flowers being fully double, round in form with high centers; and further characterized by its vigor, abundant foliage and ease of propagation from soft wood cuttings or by budding, and with an abundance of flowers.

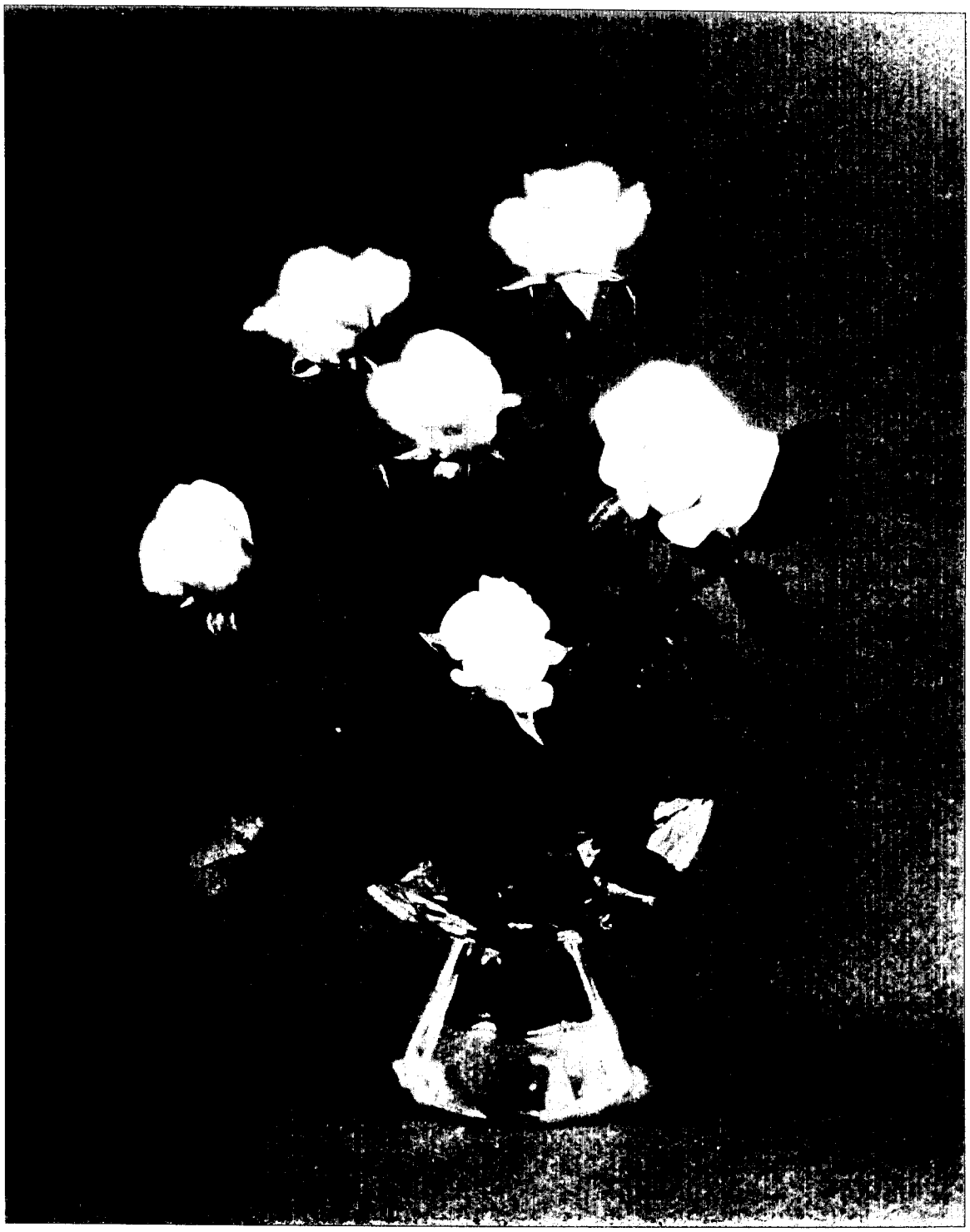

* * * * *